United States Patent [19]
Fischer et al.

[11] Patent Number: 5,637,740
[45] Date of Patent: Jun. 10, 1997

[54] PRODUCTION OF 2, 3-EPOXYPROPYL TRIALKYL AMMONIUM CHLORIDES

[75] Inventors: Wolfgang Fischer, Kahl; Manfred Langer, Karlstein; Gert Roessler, Brühl, all of Germany

[73] Assignee: Degussa Aktiengesellschaft, Frankfurt am Main, Germany

[21] Appl. No.: 400,473

[22] Filed: Mar. 8, 1995

Related U.S. Application Data

[63] Continuation of Ser. No. 136,995, Oct. 18, 1993, abandoned, which is a continuation of Ser. No. 702,301, May 20, 1991, abandoned, which is a continuation of Ser. No. 334,811, Apr. 7, 1989, abandoned, which is a continuation of Ser. No. 669,054, Nov. 7, 1984, abandoned, which is a continuation of Ser. No. 526,501, Aug. 23, 1983, abandoned, which is a continuation of Ser. No. 344,965, Feb. 2, 1982, abandoned.

[30] Foreign Application Priority Data

Feb. 4, 1991 [DE] Germany .......................... 31 03 713.5

[51] Int. Cl.$^6$ .......................... C07D 301/32; C07D 301/26
[52] U.S. Cl. .............................. 549/541; 549/521
[58] Field of Search ...................... 549/521, 541

[56] References Cited

U.S. PATENT DOCUMENTS 3,532,751  10/1970  Langher et al. .......................... 564/292

FOREIGN PATENT DOCUMENTS 1335760  10/1973  United Kingdom .

*Primary Examiner*—Ba K. Trinh
*Attorney, Agent, or Firm*—Cushman Darby & Cushman IP Group of Pillsbury Madison & Sutro LLP

[57] ABSTRACT

The reaction mixture obtained in the production of 2,3-epoxypropyltrialkylammonium chlorides by treatment of chlorohydroxypropyltrialkylammonium chlorides with alkaline acting materials in aqueous medium containing impurities which create problems in the subsequent use of the 2,3-epoxypropyltrialkylammonium chloride. According to the invention the reaction mixture is freed from these impurities by separating it from undissolved impurities by employing at least about 0.2 mole of 2,3-epoxypropyltrialkylammonium chloride per mole of water.

11 Claims, No Drawings

PRODUCTION OF 2, 3-EPOXYPROPYL TRIALKYL AMMONIUM CHLORIDES

This is a continuation application Ser. No. 08/136,995, filed on Oct. 18, 1993, which is an FWC of Ser. No. 07/702,301 filed May 20, 1991; which is an FWC of Ser. No. 07/334,811 filed Apr. 7, 1989; which is an FWC of Ser. No. 06/669,054 filed Nov. 7, 1984; which is an FWC of Ser. No. 06/526,501 filed Aug. 23, 1983; which is an FWC of Ser. No. 06/344,965 filed Feb. 2, 1982, all of which are abandoned upon the filing hereof.

BACKGROUND OF THE INVENTION

The invention is directed to a process for the purification of the reaction mixture formed in the production of 2,3-epoxypropyltrialkylammonium chlorides by the treatment of chlorohydroxypropyltrialkylammonium chlorides with alkaline acting materials in aqueous medium. The 2,3-epoxypropyltrialkylammonium chlorides for example, serve as etherifying agents for the production of cationic starch ethers. The 2,3-epoxypropyltrialkylammonium chlorides are needed in high purity particularly for this purpose. They should be free both from materials which cause side reactions and, for example, lead to cross-linking of the starch and also from materials which contaminate the starch ether in undesired manner and allow it to be separated from these materials only with considerable expense.

It is known to produce 2,3-epoxypropyltrialkylammonium salts by reaction of epihalohydrins with trialkylamines in aqueous medium and then to purify the reaction mixture by extraction or by evaporation (distillation) under reduced pressure (Paschall U.S. Pat. No. 2,876,217, the entire disclosure of which is hereby incorporated by reference and relied upon). In these processes it has not been possible to obtain the 2,3-epoxypropyltrialkylammonium salt sufficiently free from impurities, especially from cross-linking acting materials.

It is also known to carry out the reaction of the epichlorohydrin with the trialkylamines in anhydrous organic solvents, such as 1,2-dichloroethane, and to recover the 2,3-epoxypropyltrialkylammonium salt formed by crystallization from the reaction mixture (German patent 2,056,002). In this process indeed there is obtained the 2,3-epoxypropyltrialkylammonium salt in relatively pure form. However, the process is very expensive, especially long reaction times are necessary.

Besides it is known to produce 2,3-epoxypropyltrialkylammonium salts by treatment of halohydroxypropyltrialkylammonium salts with aqueous alkali, such as sodium hydroxide, and to recover the 2,3-epoxypropyltrialkylammonium salt from the reaction mixture by evaporating this to a syrup, taking the syrup up with alcohol and crystallizing the 2,3-epoxypropyltrialkylammonium salt from the alcoholic (or alcohol-acetone) medium (German AS 2055046). Therewith to obtain the epoxypropyltrialkylammonium salt in sufficient purity, several recrystallizations are necessary. The process is cumbersome and unsuited for use on an industrial scale.

SUMMARY OF THE INVENTION

There has now been found a process for the purification of the reaction mixture formed in the production of 2,3-epoxypropyltrialkylammonium chlorides by treatment of chlorohydroxypropyltrialkylammonium chlorides with alkaline acting materials in aqueous medium which is characterized by using as alkaline acting materials alkali or alkaline earth hydroxides and separating the undissolved portion from the reaction mixture having a content of at least about 0.2 mole of epoxypropyltrialkylammonium chlorides per mole of water. In a simple manner and without mentionable loss of yield with this process the reaction mixture is essentially so freed from impurities that the remaining aqueous solutions or the 2,3-epoxypropyltrialkylammonium chloride crystallized out of them can be used without further treatment, for example for the etherification of starch, to give starch ethers of outstanding quality. The process also can be readily carried out on an industrial scale.

The process of the invention is suited with advantage for the purification of reaction mixtures which are formed by the influence of alkaline acting materials on chlorohydroxypropyltrialkylammonium chlorides of the formula

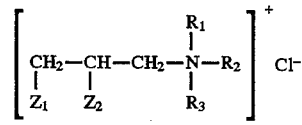

in which $Z_1$ is a chlorine atom and $Z_2$ is an OH group or conversely $Z_1$ is an OH group and $Z_2$ is a chloride atom and $R_1$, $R_2$, and $R_3$ are the same or different alkyl groups having 1 or 2 carbon atoms or $R_1$ is a methyl group and $R_2$ and $R_3$ together form an alkylene group with 4 or 5 carbon atoms. Preferably $R_1$, $R_2$, and $R_3$ are methyl groups. Illustrative of compounds which can be purified according to the invention are chlorohydroxypropyltrimethylammonium chloride, chlorohydroxypropyltriethylammonium chloride, chlorohydroxypropylmethyldiethylammonium chloride, chlorohydroxypropyldimethylethyl ammonium chloride, chlorohydroxypropylmethylpiperidinium chloride and chlorohydroxypropylmethylpyrrolidinium chloride. As alkaline acting materials for the treatment of the chlorohydroxypropyltrialkylammonium chloride there are used calcium hydroxide or barium hydroxide or preferably potassium hydroxide or most preferably sodium hydroxide.

There can be employed chlorohydroxypropyltrialkylammonium chloride of any origin, for example those which are produced according to the processes described in Noguchi U.S. Pat. No. 3,135,788, Langher U.S. Pat. No. 3,532,751, McGuire U.S. Pat. No. 3,558,501, German AS 2,055,046 and published European application 0,005,223 and for example with specifications described according to the paper of the Dow Chemical Company entitled "QUAT 188 Cationic Monomer, For Modifying Polymers to Produce Quaternary Compounds", 1978 (Form No. 192-707-78), or the paper of Degussa AG "QUAB", 3-chlor-2-Hydroxypropyltrimethylammonium chloride, Ein Kationisierungsreagenz" (Ch225-0-05-878 Vol)1. (The entire disclosure of the U.S. patents, German AS and European published application mentioned above in this paragraph are hereby incorporated by reference and relied upon. The crude chlorohydroxypropyltrialkylammonium chloride obtained especially according to Noguchi U.S. Pat. No. 3,135,788, in a given case in aqueous medium can generally be treated directly with the alkaline acting materials for the formation of the 2,3-epoxypropyltrialkylammonium chloride. Accordingly for the successful carrying out of the process of the invention there is not needed as a prerequisite the use of chlorohydroxypropyltrialkylammonium chlorides which are purified for example by recrystallization.

The chlorohydroxypropyltrialkylammonium chlorides are brought together with the alkaline acting materials in the presence of water. There can be employed the chlorohydroxypropyltrialkylammonium chloride as well as the alkaline materials at will either as aqueous solutions or as solid materials, if necessary hereby can generally be chosen as desired, but is with addition of water. The total amount of water suitably so measured that on the one hand the epoxypropyltrialkylammonium chloride in the resulting reaction mixture is completely dissolved and on the other hand its content amounts to at least 0.03 mole per mole of water.

If crude chlorohydroxypropyltrialkylammonium chlorides are employed as starting materials then they are suitably employed as dilute aqueous solutions. For this purpose there can generally be used directly the crude aqueous solutions of the chlorohydroxypropyltrialkylammonium chloride as they occur in their production, or correspondingly diluted aqueous solutions, which are prepared from crude chlorohydroxypropyltrialkylammonium chlorides. In these cases the content of epoxypropyltrialkylammonium chloride in the reaction mixtures generally amounts to about 0.03 to 0.3 mole, preferably 0.05 to 0.2 mole per mole of water. However, if pure chlorohydroxypropyltrialkylammonium chloride is used, one proceeds suitably in such manner that the reaction mixtures have higher contents, namely generally contents of about 0.05 to 0.5 mole, preferably 0.1 to 0.5 mole of the epoxypropyltrialkylammonium chloride per mole of water.

The treatment of the chlorohydroxypropyltrialkylammonium chlorides with the alkaline acting materials generally takes place suitably at temperatures between about 0° and 60° C., preferably up to 45° C., especially up to 30° C. The relative proportions of chlorohydroxypropyltrialkylammonium chloride to the alkaline acting material hereby are so chosen advantageously that at no time in the reaction mixtures is there exceeded a pH of 12.5, preferably of 12.0. Therefore there is preferred an under stoichiometric amount of alkaline acting materials rather than an over stoichiometric amount. It is especially suited to employ per equivalent of chlorohydroxypropyltrialkylammonium chloride 0.95 to 1.00 equivalent of the alkaline acting substances.

According to the invention the reaction mixture obtained in the production of the 2,3-epoxypropyltrialkylammonium chloride is purified by separating the epoxypropyltrialkylammonium chlorides at specific contents from the undissolved portions. The contents at which the separation is carried out depends to a certain extent on the type of epoxypropyltrialkylammonium chloride as well as the alkaline acting substances used and on the temperatures at which the separation takes place. Generally contents of at least about 0.2 mole per mole of water are suitable. The highest contents are a trifling below those contents at which the mixtures are saturated with dissolved epoxypropyltrialkylammonium chlorides and generally are about 0.7 mole per mole of water. Preferably the separation of the undissolved portions takes place at contents of epoxypropyltrialkylammonium chlorides in the reaction mixtures of 0.23 to 0.63 mole, especially of 0.23 to 0.55 mole per mole of water. In the separation of the undissolved portions the reaction mixtures suitably have temperatures up to about 75° C., preferably between about 10° and 60° C. There are suited for the separation processes and apparatuses which are customarily used for the separation of solids from liquids.

In a given case it is necessary in order to carry out the process of the invention to first bring the reaction mixture resulting from the treatment of the chlorohydroxypropyltrialkylammonium chloride with the alkaline acting substances to the mentioned epoxypropyltrialkylammonium content for driving off water. This suitably takes place under reduced pressure so that temperatures of at most 75° C., preferably of up to 65° C. are sufficient. When starting from dilute solutions of under about 0.1 mole content per mole of water it is particularly advantageous to select temperatures only up to about 55° C.

In the following examples (and elsewhere in the specification and claims) unless otherwise indicated all parts and percentages are by weight.

The process can comprise, consist essentially of, or consist of the recited steps with the stated materials.

EXAMPLE 1

There were evaporated in a stainless steel kettle 300 kg of a commercial aqueous solution of 3-chloro-2-hydroxypropyltrimethylammonium chloride which contained 50.6% of chlorohydroxypropyltrimethylammonium chloride (corresponding to 0.807 kmole), 2.1% of 2,3-epoxypropyltrimethylammonium chloride, 2.2% of 2,3-dihydroxypropyltrimethylammonium chloride and 4.4% of other dissolved impurities in the course of 120 minutes at a sump temperature of 46° to 65° C. and a pressure of 45 to 100 mbar so that the content of the chlorohydroxypropyltrimethylammonium chloride was 70.0%. The solution was cooled to 12° C. Then in the course of 30 minutes there were added 66.9 kg of a 47.3% aqueous sodium hydroxide solution (corresponding to 0.791 kmole of sodium hydroxide). At the beginning the addition takes place in stronger, later in weaker flow, to such an extent that the pH in the mixture always remains below 11.5. The temperature meanwhile was held at 12° to 20° C. The thus produced reaction mixture was evaporated within 150 minutes at a sump temperature of 52 to 65° C. and a pressure of 45 to 60 mbar. The content of 2,3-epoxypropyltrimethylammonium chloride then was 56.1%, corresponding to 0.44 mole per mole of water. The mixture was cooled to 20° C. and it was separated from the undissolved portions by means of a filter centrifuge. There were obtained 162 kg of filtrate which contained 70.5% of 2,3-epoxypropyltrimethylammonium chloride, 1.9% of chlorohydroxypropyltrimethylammonium chloride and 4.6% of 2,3-dihydroxypropyltrimethylammonium chloride. The solution of epoxypropyltrimethylammonium chloride obtained as filtrate was so pure that it could be employed directly as etherifying agent for the production of cationic starch ethers. Besides, there were obtained 55.5 kg of filter residue This contained 46.2 kg (0.79 kmole) of sodium chloride. The residue was washed with water; the washing liquid, which contains epoxypropyltrimethylammonium chloride and chlorohydroxypropyltrimethylammonium chloride, was utilized in subsequent batches. In the average of several batches the yield of material effective for the etherification was 97.1%.

EXAMPLE 2

There were evaporated 438.5 kg of a commercial aqueous solution of 3-chloro-2-hydroxypropyltrimethylammonium chloride which contained 50.6% of chlorohydroxypropyltrimethylammonium chloride (corresponding to 1.178 kmole), 1.8% of 2,3-epoxypropyltrimethylammonium chloride, 1.8% of 2,3-dihydroxypropyltrimethylammonium chloride, and 4.5% of other dissolved impurities, in the course of 45 minutes at a sump temperature of 57° to 62° C. so that the content of the chlorohydroxypropyltrimethylammonium chloride was 58.0%. The solution was cooled to 23° C., then in the course of 40 minutes while the temperature was held to 23° to 30° C. there were added 96.7kg of a 47.3% aqueous sodium hydroxide solution (corresponding to 1.143 kmole of sodium hydroxide) in such manner that the pH in the mixture always does not exceed 11.8. The pH at the end was 10.7. The reaction mixture produced contained 37.2% of 2,3-epoxypropyltrimethylammonium chloride, 2.2% of chlorohydroxypropyltrimethylammonium chloride and 2.0% of 2,3-dihydroxypropyltrimethylammonium chloride as well as 13.8% of sodium chloride. The mixture was evaporated in the course of 25 minutes at a sump temperature of 55° to 65° C. and a pressure of 45 to 90 mbar so that the content of 2,3-epoxypropyltrimethylammonium chloride was 52.8% corresponding to 0.32 mole per mole of water. After cooling to 30° C. the undissolved portions were separated off by means of a filter centrifuge. There were obtained 250 kg of filtrate which contained 66.4% of 2,3-epoxypropyltrimethylammonium chloride, 4.2% of chlorohydroxypropyltrimethylammonium chloride and 4.9% of 2,3-dihydroxypropyltrimethylammonium chloride. The solution of epoxypropyltrimethylammonium chloride obtained as filtrate was so pure that it could be employed directly as etherifying agent for the production of cationic starch ethers. Besides there were obtained 75.8 kg of filter residue. This contained 66.6 kg (1.14 kmole) of sodium chloride. The residue was washed with water; the washing liquid, which contains epoxypropyltrimethylammonium chloride and chlorohydroxypropyltrimethylammonium chloride, was utilized in subsequent batches. In the average of several batches the yield of material effective for the etherification was 96.6%.

EXAMPLE 3

To a mixture of 2685 grams of a 71% aqueous solution of trimethylamine hydrochloride (corresponding to 20 mole) and 2330 grams of water there were added in uniform flow in the course of 5 hours 1885 grams (20 moles) of epichlorohydrin. The mixture meanwhile was held at 35° C. and then for 2 hours at 30° C. Then it contained 42.6% of 3-chloro-2-hydroxypropyltrimethylammonium chloride, 4.6% of 1,3-dichloropropanol-2, 2.5% of 2,3-epoxypropyltrimethylammonium chloride, 0.2% of 2,3-dihydroxypropyltrimethylammonium chloride, 5.9% of other dissolved impurities and 10.4% of chlorine as chloride.

The pH of the mixture was 7.6, 3300 grams of the mixture (corresponding to 7.46 moles of chlorohydroxypropyltrimethylammonium chloride) within one-half hour was treated with 592 grams of 50% aqueous sodium hydroxide solution (corresponding to 7.40 moles of sodium hydroxide) in such manner that the pH did not exceed 11.5. The temperature meanwhile was held at 20° C. The reaction mixture at a sump temperature from initially 20° C. to finally 40° C. and pressure of 15 to 20 mbar was evaporated to such an extent that the content of 2,3-epoxypropyltrimethylammonium chloride was 55.6%, corresponding to 0.43 mole per mole of water. Then the undissolved portions were filtered off. There were obtained 1525 grams of filtrate which contained 70.7% of 2,3-epoxypropyltrimethylammonium chloride, 2.3% of chlorohydroxypropyltrimethylammonium chloride, and 1.5% of 2,3-dihydroxypropyltrimethylammonium chloride. The content of epichlorohydrin as established by gas chromatographic determination was 24 ppm. The solution was so pure that it could be employed directly as etherifying agent for the production of cationic starch ethers. Besides there were recovered 445 grams of filter residue. This contained 430 grams (7.4 moles) of sodium chloride.

EXAMPLE 4

315.0 grams of 60% aqueous solution of 3-chloro-2-hydroxypropyltrimethylammonium chloride (corresponding to 1.00 mole) were reacted with 110.5 grams of 50% aqueous potassium hydroxide solution (corresponding to 0.99 mole of potassium hydroxide). Within one hour there were driven off from this mixture at sump temperatures of 45° to 60° C. 202 grams of water. The reaction mixture was separated from the undissolved portions by filtration. The filtrate contained 67.0% of 2,3-epoxypropyltrimethylammonium chloride, 1.4% of chlorohydroxypropyltrimethylammonium chloride, and 0.6% of potassium chloride. The solution was so pure that it could be employed directly as etherifying agent for the production of cationic starch ethers. There were recovered with the undissolved portions 98.3% of the potassium chloride formed in the reaction.

The entire disclosure of German priority application P 3103713.5 is hereby incorporated by reference.

What is claimed is:

1. A process for the purification of the reaction mixture obtained in the production of 2,3-epoxypropyltrimethylammonium chloride by treatment of chlorohydroxypropyltrimethylammonium chloride with an alkaline acting material in aqueous medium and in which an undissolved portion is formed comprising employing as the alkaline acting material an alkali metal hydroxide or an alkaline earth metal hydroxide, the ratio of alkaline acting material to the chlorohydroxypropyltrimethylammonium chloride during the reaction being so selected that the pH never exceeds 12.5 and separating the aqueous reaction mixture having a content of from about 0.2 to 0.7 mole of epoxypropyltrimethylammonium chloride per mole of water during the separation.

2. A process according to claim 1 wherein the reaction mixture contains 0.23 to 0.63 mole of epoxypropyltrimethylammonium chloride per mole of water during the separation.

3. A process according the claim 2 wherein the separation is carried out at a temperature of 10° to 55° C.

4. A process according the claim 1 wherein the separation is carried out at a temperature of 10° to 75° C.

5. A process according to claim 4 wherein the temperature is 10° to 65° C.

6. A process according to claim 4 wherein the temperature is 10° to 60° C.

7. A process according to claim 1 wherein the reaction mixture contains about 0.23 to 0.55 mole of epoxypropyltrimethylammonium chloride per mole of water.

8. A process according to claim 1 wherein the pH never exceeds 12.0.

9. In a process for the manufacture of 2,3-epoxypropyltrimethylammonium chloride which consists essentially of reacting chlorohydroxypropyltrimethylammonium chloride with an alkaline acting material in an aqueous medium, the improvement for producing a more highly purified product which comprises using as the alkaline acting material, a member of the group consisting of alkali metal hydroxides and alkaline earth metal hydroxides, controlling the rate of mixing the chloropropyltrimethylammonium chloride and the alkaline acting material so that pH never exceeds 12.5, adjusting the concentration of 2,3-epoxypropyltrimethylammonium chloride in the aqueous medium so that the reaction mixture contains from about 0.2 to 0.7 moles of epoxypropyltrimethylammonium chloride per mole of water and separating the aqueous reaction mixture from the undissolved residue contained therein.

10. A process for producing a purified 2,3 epoxypropyltrimethylammonium chloride product comprising, a) adding to an aqueous solution of chlorohydroxypropyltrimethyl ammonium chloride an alkali metal hydroxide or an alkaline earth metal hydroxide to form a reaction mixture containing 2,3 epoxypropyltrimethylammonium chloride, wherein the addition is performed in a controlled manner such that the pH never exceeds 12.5 and the final concentration of the alkali metal hydroxide or the alkaline earth metal hydroxide is less than or equal to the stoichiometric amount needed for the formation of the 2,3 epoxypropyltrimethylammonium chloride, b) removing water from the reaction mixture of step a) at a temperature of at most 75° C. and under reduced pressure until the epoxypropyltrimethylammonium chloride in the reaction mixture is between 0.23 and 0.63 moles per mole of water, and c) separating 2,3 epoxypropyltrimethylammonium chloride product from the reaction mixture of step b), which contains undissolved portions, to form the purified 2,3 epoxypropyltrialkylammonium chloride product.

11. A process for the purification of the reaction mixture obtained in the production of 2,3 epoxypropyltrimethylammonium chloride according to claim 1 wherein the ratio of alkaline acting material to the chlorohydroxypropyltrimethyl ammonium chloride is equal to or less than the stoichiometric amount needed for the formation of 2,3 epoxypropyltrimethyl ammonium chloride.

* * * * *